United States Patent [19]

Haller

[11] 4,198,975
[45] * Apr. 22, 1980

[54] SELF-INJECTING HYPODERMIC SYRINGE DEVICE

[76] Inventor: J. Gilbert Haller, 2120 New Holland Pike, Lancaster, Pa. 17601

[*] Notice: The portion of the term of this patent subsequent to Jan. 10, 1995, has been disclaimed.

[21] Appl. No.: 949,245

[22] Filed: Oct. 6, 1978

[51] Int. Cl.$^2$ ............................................. A61M 5/00
[52] U.S. Cl. .............................. 128/218 A; 128/218 F
[58] Field of Search ............... 128/218 A, 218 F, 215, 128/217, 234

[56] References Cited

U.S. PATENT DOCUMENTS

| | | | |
|---|---|---|---|
| 2,816,546 | 12/1957 | Luhmann | 128/218 F |
| 2,892,457 | 6/1959 | Sturtz | 128/218 F |
| 2,942,603 | 6/1960 | Geyer | 128/235 |
| 3,064,650 | 11/1962 | Lewis | 128/218 A |
| 4,067,334 | 1/1978 | Haller | 128/218 A |
| 4,154,239 | 5/1979 | Turley | 128/217 |

FOREIGN PATENT DOCUMENTS 1242060 8/1968 United Kingdom ................ 128/218 A

*Primary Examiner*—John D. Yasko
*Attorney, Agent, or Firm*—C. Hercus Just

[57] ABSTRACT

A hypodermic syringe which is self-injected has a substantially T-shaped frame of which the stem depends from the top portion to comprise a handle and a syringe carriage slides along said top portion initially by means of a tension spring. A sear holds the carriage retracted against the spring but, when released, the spring shoots the syringe and carriage forwardly a limited distance adequate to inject the needle of the syringe into flesh. A finger-operated trigger, of which two embodiments are provided, when pushed inwardly into the handle actuates a sear release during the short initial movement of the trigger and continued movement thereof moves a slide forwardly along the top of the frame against the outer end of the syringe plunger by means of motion-multiplying means to provide greater movement of said slide for a much lesser movement of said trigger.

7 Claims, 7 Drawing Figures

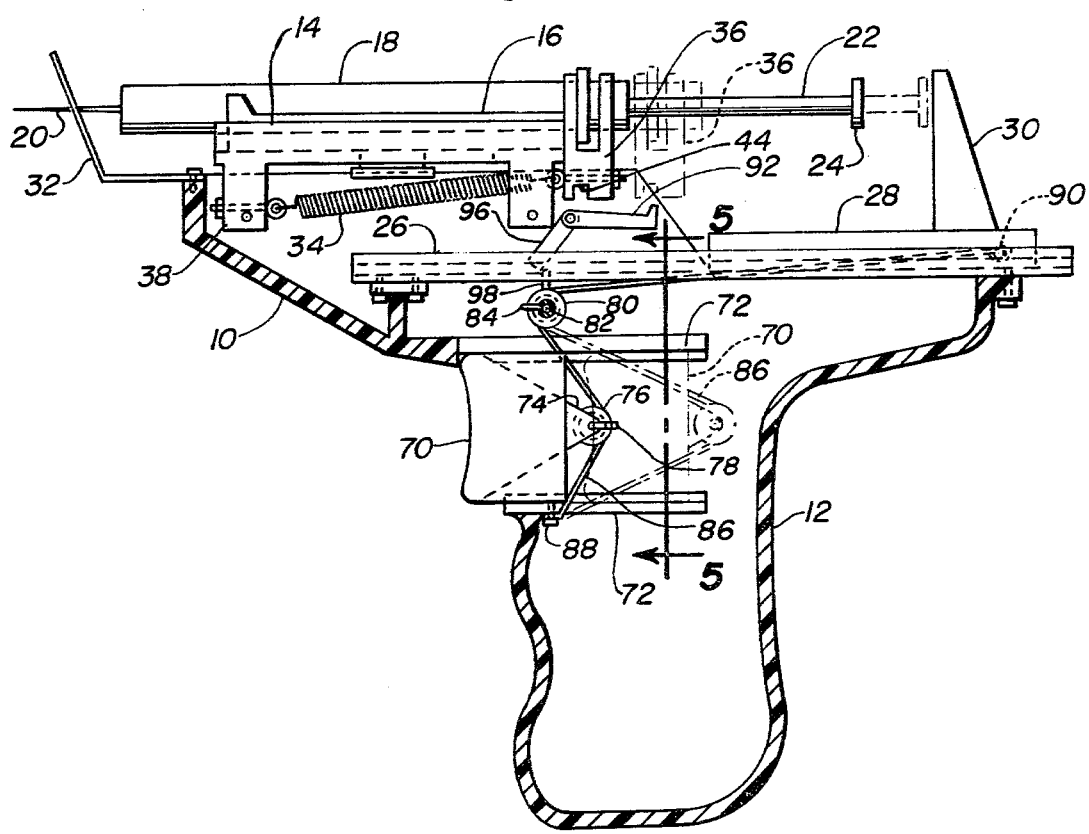

SELF-INJECTING HYPODERMIC SYRINGE DEVICE

BACKGROUND OF THE INVENTION

The present invention essentially comprises an improvement over the applicant's prior U.S. patent, No. 4,067,334, issued Jan. 10, 1978, and in which T-shaped frame, of which the stem comprised a handle, supported a slide along the top of the frame in which a hypodermic syringe was detachably mounted for quick initial injection of the needle of the syringe into the flesh by means of a spring which effected only such limited initial movement very rapidly. An additional slide movable along the top of the frame was actuated by a fluid-operated piston in a cylinder, one end of the cylinder being connected to a squeezable bulb which injected fluid in said end of the cylinder to move the plunger forwardly for engagement with the handle of the syringe to effect discharge of the contents of the syringe after the needle had been inserted into the flesh.

It has been found that this prior device, while mechanically satisfactory, rendered movement of the plunger of the fluid-operated unit relatively slow, in addition to requiring said fluid-operated cylinder unit which consumed a certain amount of space and also rendered the entire unit somewhat more complex than was desirable. Accordingly, additional research and contemplation has resulted in the present invention in which said fluid-operated cylinder unit and the compressible bulb has been eliminated and several embodiments of rapidly-operated motion-multiplying means have been substituted for the aforementioned cylinder unit and compressible bulb which also has resulted in rendering the structure capable of being made in a somewhat smaller size than that of the prior patent and, in addition, the actuation by the motion-multiplying means referred to renders the movement of the hypodermic cylinder more direct and positive than that afforded by the squeezable bulb due to employing several embodiments of trigger-type means which actuate the motion-multiplying mechanisms.

The use of tripper-type mechanisms in self-injecting type syringe devices is not new and examples of such devices are found in the following prior U.S. patents: Nos.

2,816,546 Luhmann Dec. 17, 1957
2,892,457 Sturtz June 30, 1959
2,942,603 Geyer June 28, 1960
3,064,650 Lewis Nov. 20, 1962
1,242,060 (British)—Published Aug. 6, 1968

None of the structures illustrated in the above-cited patents include motion-multiplying mechanism which operates between the trigger of the device and the carriage which moves the plunger-actuating member forward to discharge the contents of the hypodermic syringe. In fact, the patent to Geyer has a gear-type motion-changing device which actually produces a slower motion of the plunger than that of the trigger, whereby the operation is the reverse of that of the present invention.

SUMMARY OF THE INVENTION

It is the principal object of the present invention to provide in a self-injecting hypodermic syringe device several embodiments of trigger mechanism associated with the handle of the frame and operable respectively in a direct sliding movement and in a pivotal movement to actuate motion-multiplying mechanism extending between the trigger and the slide which carries the plunger-operating member, whereby movement of the trigger is multiplied at least twice, in accordance with the principle of operation of pulleys, when imparted to the plunger-operating slide and, in the second embodiment, which includes a pivoted trigger, an even greater amount of multiplied motion is produced in the plunger-operating slide.

It is another object of the invention to include in conjunction with the motion-multiplying mechanism, means which releases the sear that normally holds the slide which supports the hypodermic syringe in retracted position and, through the action of a tension spring, when the sear is released from said slide, the spring shoots the hypodermic syringe on said carriage forwardly very rapidly to effect penetration of flesh by the needle of the syringe, said insertion being of a relatively short stroke of predetermined dimension prior to the movement of the trigger effecting feeding movement of the slide for the plunger-operating member through the medium of the motion-multiplying mechanism.

A still further object of the invention is to provide motion-multiplying mechanism which is of a positive mechanical type having no variable forces as is characteristic of squeezable bulbs as in applicant's prior hypodermic syringe device.

Details of the foregoing objects and of the invention, as well as other objects thereof, are set forth in the following specification and illustrated in the accompanying drawings comprising a part thereof.

BRIEF DESCRIPTION OF THE DRAWINGS

FIG. 4 is a view similar to FIG. 1, but showing a second embodiment of trigger and motion-multiplying mechanism.

FIG. 5 is a fragmentary vertical sectional view of the embodiment shown in FIG. 4, as seen on the line 4—4 thereof.

FIG. 6 is a fragmentary detailed elevation showing the sear which normally retains the syringe-carrying slide, the holding position of the sear being shown in full lines in said figure, and in phantom, the release position being illustrated in conjunction with the portion of the motion-multiplying mechanism which actuates the sear.

FIG. 7 is a fragmentary vertical elevation of a portion of the mechanism shown in FIG. 6, as seen on the line 7—7 thereof.

DETAILED DESCRIPTION

In view of the fact that the present invention to a large extent comprises an improvement over applicant's prior U.S. patent, No. 4,067,334, in order to simplify and limit the description of details of the present invention, certain references to similar portions of the prior patent and present invention will be indicated for reference to the prior patent, particularly since one of the principal features of the present invention comprises substituting for the squeezable bulb and fluid-operated plunger and piston unit which operates the plunger-actuating slide, a motion-multiplying mechanism which is actuated by a movable trigger in the handle and is connected to the plunger-operating slide, not only to permit limited movement of the trigger to effect much more extensive movement of the plunger-operating slide, but also provide a more positive actuation of said slide by the trigger than in depending upon a compressible fluid to effect the same, as in said prior patent.

The present invention also includes two embodiments of motion-multiplying means which respectively are illustrated in FIGS. 1–3 and FIGS. 4–7, both of said embodiments employing pulleys around which an inelastic flexible member extends, which preferably comprises a relatively narrow metallic tape, opposite ends of the flexible member being fixedly attached respectively to a portion of the handle and the plunger-operating slide. The arrangement of the flexible member relative to the pulleys comprises a tackle type arrangement to effect such multiplication of movement. This effect is similar to that employed in hoisting mechanism in which ropes or cables, for example, extend upwardly around a pulley and down the other side therefrom, in which event when a single pulley is employed and one end of the cable or rope is fixed, movement of the pulley is substantially one-half the movement of the opposite end of the rope or cable. In adapting such principle to the present invention, however, innovations have been required in order to effectively accommodate such tackle type principles within the small confines of a manually-engageable handle and handle frame for said syringe-injecting device, details of which are set forth hereinafter.

Figure 1:
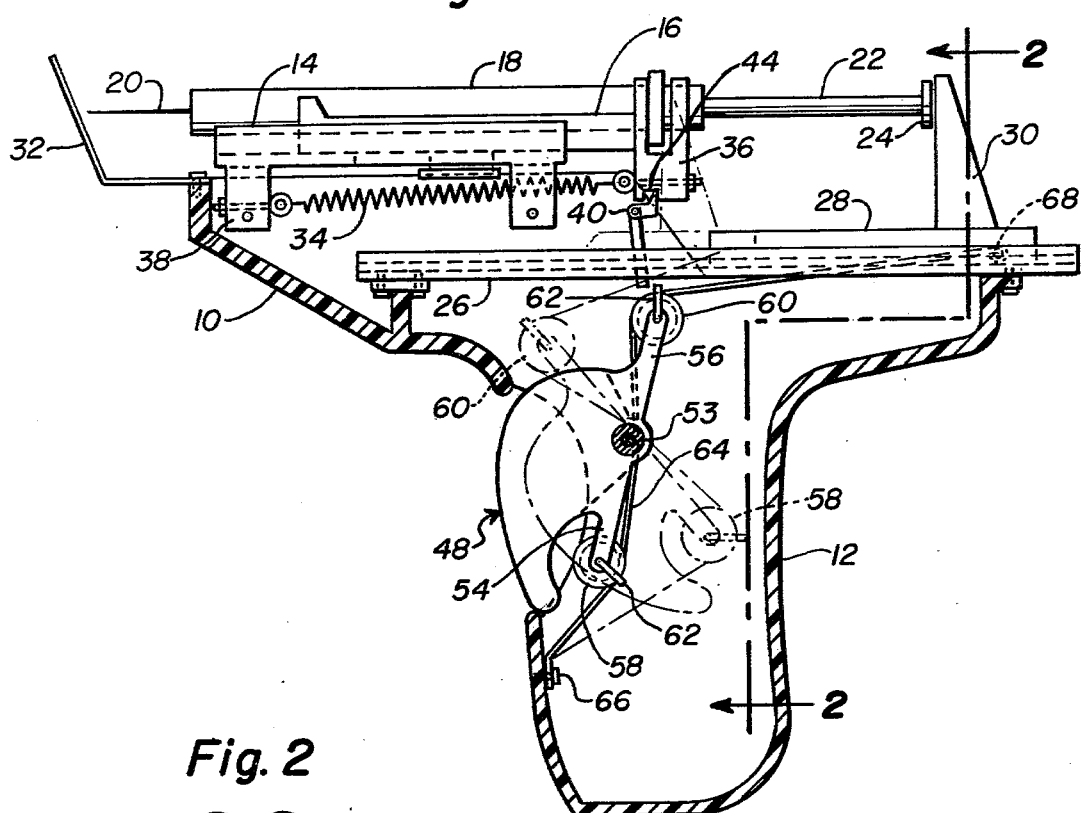
FIG. 1 is a side elevation, partly in vertical section to disclose details of the mechanism of the device and illustrating in full line the initial starting position of the trigger and the motion-multiplying means actuated thereby and, in phantom, showing substantially the maximum extent of movement of the plunger-operating slide by the motion-multiplying mechanism.
Figure 2:
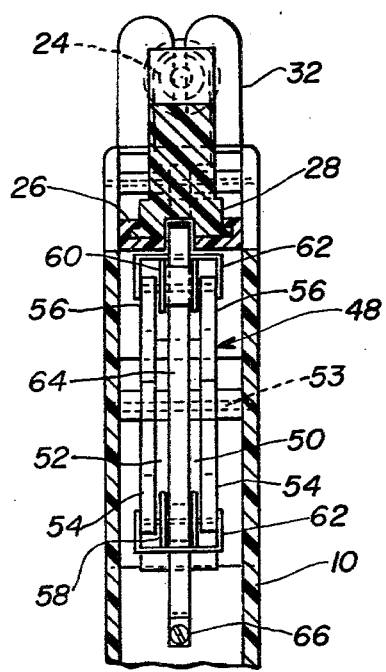
FIG. 2 is a fragmentary vertical sectional view of the device shown in FIG. 1, as seen on the line 2—2 thereof.
Figure 3:
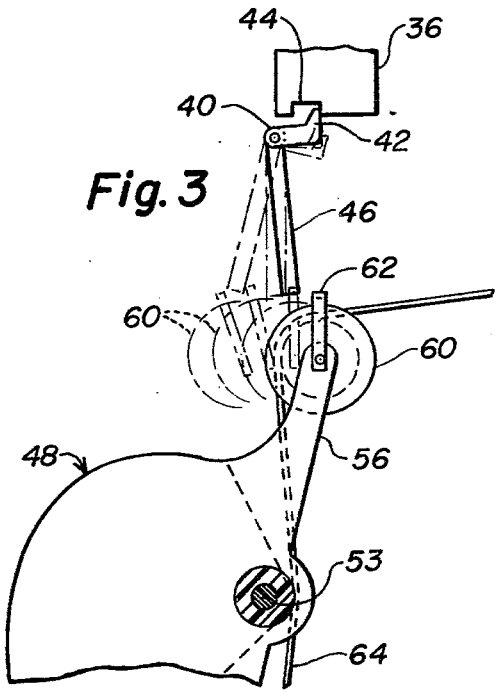
FIG. 3 is a fragmentary side elevation illustrating on a larger scale than in the preceding figures, the means by which the sear is operated which normally holds the syringe-carrying carriage in initial, retracted position, the retaining position of the sear being shown in full lines in said figures and, in phantom, the released position thereof being illustrated.

Referring to the embodiment of the invention shown in FIGS. 1–3, said device includes a handle frame 10, which, as seen from FIG. 1, is substantially T-shaped in side view, the upper portion thereof extending horizontally with respect to a depending handle 12 per se. The handle frame 10 and the handle 12 may be made unitarily by molding, for example, from suitable plastics, metal or any other appropriate material. Said handle frame and handle also are hollow, the frame 10 supporting a sub-frame 14, comprising a guide for a slide 16 which supports a hypodermic syringe 18, having a needle 20 on one end and a plunger rod 22 on the opposite end terminating in a button 24.

The handle frame 10 also contains a second sub-frame comprising a guide 26 along which a plunger-operating slide 28 is guided for movement, the slide 28 having an upstanding projection 30 thereon which engages the button 24 of the plunger rod 22 of syringe 18.

As in applicant's prior patent, the initial operation of the device effects an instantaneous injection of the needle 20 into the flesh of a user by extending the same past the angular shoe 32 which is slotted to permit such movement and this movement of the syringe, which is detachably held by the guide 14 is effected by a spring 34 of the tension type connected respectively between a positioning boss 36 on slide 16 and a fixed member 38 within the handle frame 10 adjacent the forward end thereof.

When the carriage 14 and the syringe 18 thereon is in the retracted position, the spring 34 is under tension and said position is maintained by a pivoted sear 40, the pivotal axis of the sear being fixed within the handle frame 10 and said sear having an upstanding terminal end 42, see FIG. 3, which is received within a notch 44 in the positioning boss 36. The sear also has a depending tail 46 for purposes to be described. The guide 14 and syringe 18, in the initial position thereof, is as illustrated in FIG. 1. The slide 14 is moved to said position manually from an extended, injecting position, not illustrated, during which time the spring 34 is tensioned and the end 42 of sear 40 is disposed within the notch 44. Any suitable spring means, not shown, such as, for example, the spring means shown in applicant's prior patent with respect to the sear illustrated therein, may be employed to maintain the depending tail 46 substantially in the position shown in FIGS. 1 and 3.

It will be understood that the handle frame 10, for example, may be made in two parts which engage each other along a central plane, thereby contributing to the assembly of the various elements which are contained within the interior of the handle frame 10, such as the trigger 48, which may be made of suitable metal, plastics, or otherwise and the shape thereof is shown in full lines in FIG. 1. Said trigger preferably comprises a pair of similar plates 50 and 52, which are shown in FIG. 2 and comprise a unitary assembly for trigger 48. A pivot 53 extends between the opposite sides of the housing frame 10 and pivotally supports the trigger 48, especially for movement of the lower portions thereof between the initial, inoperative position shown in full lines in FIG. 1 and the fully recessed movement thereof which is shown in exemplary manner in phantom in FIG. 1. Such movement is counterclockwise. Each of the plates 50 and 52 of trigger 48 have arms 54 and 56 between which pivots extend respectively for supporting pulley wheels 58 and 60. U-shaped bails 62 extend between the pairs of arms 54 and 56 adjacent the peripheries of the pulley wheels 58 and 60 for purposes of preventing separation therefrom of an elongated flexible member 64 which preferably comprises a relatively narrow metal tape, such as stainless steel or the like. One end of the flexible member 64 is fixed securely by a pin 66 to the interior of the lower portion of the handle 12 and the opposite end 68 thereof is securely fixed to the plunger-operating slide 28, preferably adjacent the outermost end thereof. Member 64 extends partially around the circumference of pulley wheel 58 and then upwardly past pivot 54 and partially around the circumference of the upper pulley wheel 60. The bails 62 respectively associated with said pulley wheels extend over the members 64 so as to insure that said member will always remain in engagement respectively with said pulley wheels, which, in addition, are grooved so as further to insure operative engagement between the member 64 and said pulley wheels, the flanges being best shown in FIG. 2.

In the operation of the embodiment of the invention shown in FIGS. 1–3, particularly with reference to FIG. 1, it will be seen that when the trigger 48 is pivotally moved counterclosewise, it will move the pulleys 58 and 60 respectively to the phantom position shown in exemplary manner in FIG. 1, and in so doing, will perform the motion-multiplying effect of the tackle type referred to hereinabove, and result in limited inward movement of the trigger 48 producing a much greater linear movement of the plunger-operating slide 28 and its projection 30 for purposes of discharging the contents of the syringe 18 which has previously been injected into flesh during the initial movement of trigger 48 by release of the sear 40 relative to notch 44. Such release is accomplished by the following mechanism.

The bail 62 associated with the upper ends of the arms 56 of trigger 48 and also extending across the periphery of the pulley wheel 60 is positioned with respect to the terminal end of the depending tail 46 of sear 40, as shown best in FIG. 3, so that during the initial counterclockwise movement of the trigger 48, the bail 62 acts as a projection which engages the terminal end of the tail 46 and moves the upstanding terminal end 42 thereof from the notch 44 and permits the slide 16, which carries the syringe 18 to move forwardly instantly by the action of spring 34 and inject the needle 20 into the flesh of the user, as aforesaid. When the device is removed from the patient by withdrawing the needle 20 from the flesh, the device may be restored to its initial position by manually engaging projection 30, for example, to retract the plunger-operating slide 28 to starting position and this will result in the trigger 48 also being restored to its initial, full line position shown in FIG. 1. Then the slide 16 may be manually retracted to re-engage the sear 40 with the notch 44. This may be accomplished either when the device is supporting the hypodermic syringe 18 or without the same being mounted thereon.

Referring to FIGS. 4-7, in which the second embodiment of the motion-multiplying means is illustrated, the basic mechanism is the same as that shown in the embodiment of FIGS. 1-3, with the exception of the motion-multiplying means per se. Accordingly, where the various elements of the two embodiments are the same, the same reference characters are employed, especially in FIGS. 1 and 4.

Referring to FIG. 4, the trigger 70 is slidable between a pair of parallel guideways 72 and preferably includes a pair of transversely-spaced ears 74 between the innermost ends of which a pulley wheel 76 is mounted, said pulley wheel also having a bail 78 extending across the periphery thereof. Another pulley wheel 80 is supported upon a shaft 82 which extends between opposite sides of the handle frame 10, as best shown in FIG. 5, the shaft preferably is stationary and opposite ends of the U-shaped bail 84 are connected to the shaft and the intermediate portion thereof extends across the periphery of the pulley wheel 80, as clearly shown in FIG. 4.

An elongated flexible member 86 which is similar to the member 64 in the preceding embodiment is fixedly connected at one end 88 to a fixed part of the handle 12, such as the lower guideway 72, for example, and said member extends around a portion of the periphery of the pulley wheel 76 on trigger 70, and then upwardly and around a portion of the periphery of the pulley wheel 80, which is rotatable about a stationary axis, and then continues on to be connected at the opposite end 90 to the plunger-operating slide 28, as shown in FIG. 1. It will be seen that the member 86 extends around relatively opposite sides on the pulley wheels 76 and 80, as is also the situation in regard to the first embodiment with respect to the lower pulley wheel 58 and the upper pulley wheel 60. Accordingly, when the trigger 70 is moved inwardly to the phantom position thereof, the pulley wheel 76 on the inner end thereof will move the flexible member 86 substantially to the phantom position thereof, shown in FIG. 1, and in so doing will effect a much greater linear movement of the plunger-operating slide 28, due to the multiplying motion effect of the arrangement afforded by the pulleys 76 and 80 and the manner in which the member 86 extends partially around the same.

In order to effect the initial insertion of the needle 20 which is shown in the extended position in FIG. 4, as distinguished from the retracted, initial position thereof, and in which the rearend of the syringe 18 and also the positioning boss 36 are shown in phantom, in FIG. 4, a pivoted sear 92 is shown in FIG. 4 in the retracted position but it will be understood that the terminal extremity 94 thereof, see FIG. 6, will be disposed in notch 44 of the positioning boss 36, and will be retained therein by an appropriate spring, not shown, as in regard to the sear 40 in the preceding embodiment. When the sear is released from the notch 44, the spring 34 will instantly inject the needle 20 into flesh by the operation of tension spring 34. Release of the sear from the notch 44 is effected by a tail 96 thereon, shown best in FIG. 6 on a larger scale and as viewed from the opposite side from that shown in FIG. 4, by means of a lug 98, which is fixed to one flange of the pulley wheel 80, best shown in detail in FIGS. 6 and 7, which engages the lower end of the tail 96, as shown in FIG. 6, when the pulley is moving clockwise as viewed in FIG. 6, but which movement would be counterclockwise as viewed in FIG. 4, and thus effect disengagement of the terminal extremity 94 of sear 92 from the notch 44 and permit the injection movement of the needle 20 as aforesaid.

Retraction of the slides 16 and 28 to initial starting position is effected manually as described above relative to the proceding embodiment illustrated in FIGs. 1-3.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

I claim:

1. A portable device for holding a loaded hypodermic syringe and effecting an instantaneous injection of the needle of the syringe into the flesh followed by operation of the plunger of the syringe, said device comprising in combination, a handle frame having forward and rearward end portions, a longitudinal guideway on said handle frame adjacent said forward end portion, a syringe slide movable along said guideway, means on said slide to support a syringe having a needle on one end and a plunger knob on the other, a spring connected between said syringe slide and handle frame, a sear engageable with said syringe slide and operable to secure the same in a retracted position in said guideway, and a handle depending from said handle frame, in combination with a trigger supported upon said handle for movement toward said handle and from the interior thereof, a second guideway upon said handle frame adjacent the rearward portion thereof and parallel to said longitudinal guideway, a plunger-operating slide movable upon said second guideway toward and from said longitudinal guideway and including means engageable with said plunger knob when moving toward said longitudinal guideway to push the plunger into the syringe, and motion-multiplying mechanism connected between said trigger element and said plunger-operating slide operable upon initial movement of said trigger toward said handle to release said sear to effect injection of said needle into the flesh of the user, and continued movement of said trigger further actuating said motion-multiplying means to move said plunger-operating slide positively and at a substantially greater distance than the travel of said trigger toward said handle.

2. The device according to claim 1 in which said motion-multiplying means comprises an elongated flexible member connected at opposite ends respectively to said trigger and plunger-operating slide, and movable means on said trigger around which said flexible member at least partially extends to effect a tackle type multiplication of movement of said plunger-operating slide relative to the movement of said trigger.

3. The device according to claim 2 in which said movable means on said trigger comprises a pulley and said flexible member is inelastic and extends partially around said pulley on said trigger.

4. The device according to claim 3 in which said trigger is slidably supported for movement between positions respectively extended beyond said handle and at least partially recessed within said handle, and a second pulley included within said handle frame above the upper end of said handle and rotatable about a stationary axis in said handle frame, said flexible member extending around said second pulley for a substantial portion of the circumference thereof to provide said tackle type multiplication of movement of said plunger-operating slide.

5. The device according to claim 4 in which said pulley on said trigger is carried by the end of said trigger which is movable into said handle and engages the opposite surface of said flexible member from that which extends around the pulley on the axis in said handle frame, thereby to further increase the multiplication of movement of said plunger-operating slide relative to the movement of said trigger.

6. The device according to claim 3 in which said trigger is pivotally movable about a pivot in said handle, one portion of said trigger projecting through an opening in one side of said handle and another portion being within said handle and having a pair of pulleys rotatably mounted thereon in oppositely spaced positions from the pivotal axis of said trigger, and said flexible member extending between and respectively partially around opposite circumferential portions of said pulleys, whereby inward movement of said one portion of said trigger toward said handle moves said pulleys simultaneously toward opposite edges of said handle to effect said tackle type multiplication of movement of said plunger-operating slide.

7. The device according to claim 2 in which said elongated flexible member comprises an inelastic tape extending around said handle frame and said pulley being rotated by said tape when said trigger is moved inwardly toward said handle, said device also including a projection on said pulley and said sear being pivotally mounted within said handle frame, and said sear having a portion thereon extending into the path of movement of said projection on said pulley when said sear is in engagement with said syringe slide, whereby initial movement of said trigger inwardly toward said handle rotates said pulley in a direction to engage said portion of said sear by said projection on said pulley and move the sear from engagement with said syringe slide to effect injecting movement of said syringe by said spring connected to said slide.

* * * * *